United States Patent [19]

Hlavka et al.

[11] Patent Number: 4,670,458

[45] Date of Patent: Jun. 2, 1987

[54] HYDROXYLATED 1,2-DIAMINOCYCLOHEXANE PLATINUM COMPLEXES

[75] Inventors: Joseph J. Hlavka, Tuxedo Park; Yang-I Lin, Nanuet; Panayota Bitha, Pomona, all of N.Y.

[73] Assignee: American Cyanamid Company, Stamford, Conn.

[21] Appl. No.: 824,479

[22] Filed: Jan. 31, 1986

[51] Int. Cl.[4] ............................................. C07F 15/00
[52] U.S. Cl. ..................................... 514/492; 556/137
[58] Field of Search .......................... 556/137; 514/492

[56] References Cited

U.S. PATENT DOCUMENTS

| | | | |
|---|---|---|---|
| 4,119,654 | 10/1978 | Tobe et al. | 556/137 |
| 4,140,707 | 2/1979 | Cleare et al. | 556/137 |
| 4,284,579 | 8/1981 | Meischen et al. | 556/137 X |
| 4,500,465 | 2/1985 | Amundsen et al. | 556/137 X |
| 4,567,285 | 1/1986 | Kidani et al. | 556/137 |
| 4,587,331 | 5/1986 | Hlavka et al. | 556/137 X |

FOREIGN PATENT DOCUMENTS 1380228  1/1975  United Kingdom .

*Primary Examiner*—Helen M. S. Sneed
*Attorney, Agent, or Firm*—Edward A. Conroy, Jr.

[57] ABSTRACT

This disclosure describes platinum complexes of $3\beta,4\alpha$-diamino-$1\alpha,2\alpha$-cyclohexanediol which possess the property of inhibiting the growth of tumors in mammals.

8 Claims, No Drawings

HYDROXYLATED 1,2-DIAMINOCYCLOHEXANE PLATINUM COMPLEXES

SUMMARY OF THE INVENTION

This invention is concerned with the new organic compound 1-α,2-α,3-β,4-α)-3,4-diamino-1,2-cyclohexanediol having the structure:

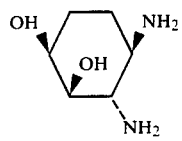

and with platinum complexes made from the above compound having the formulae:

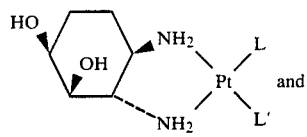

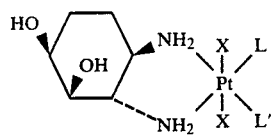

wherein L and L' are selected from the group consisting of halide, nitrate, sulfate and a monobasic carboxylate such as acetate or hydroxy acetate, or L or L' taken together may be a dibasic carboxylate selected from the group consisting of

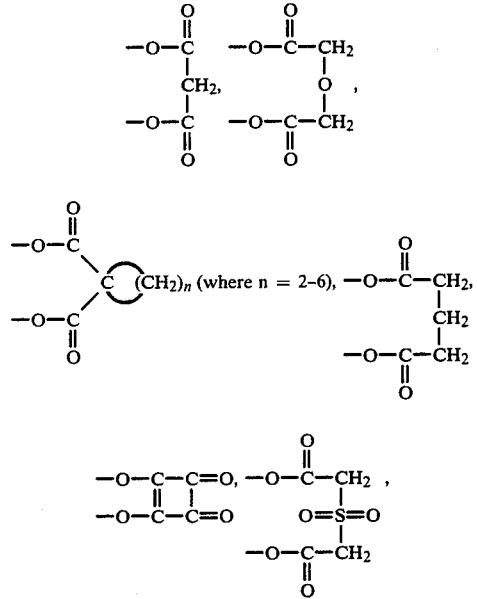

oxalic acid, methylmalonic acid, succinic acid, or L and L' taken together may be a tribasic carboxylate selected from the group consisting of

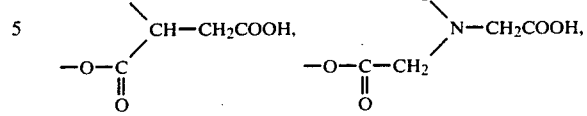

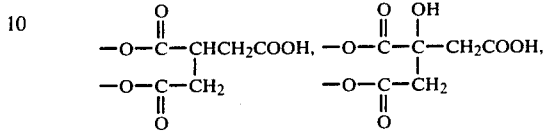

and

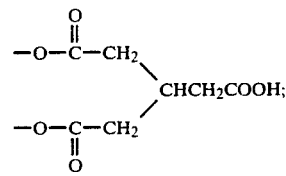

and X is selected from the group consisting of halogen and hydroxy.

DETAILED DESCRIPTION OF THE INVENTION

The compounds of this invention may be prepared according to the following reaction schemes.

Scheme I

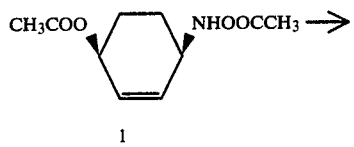

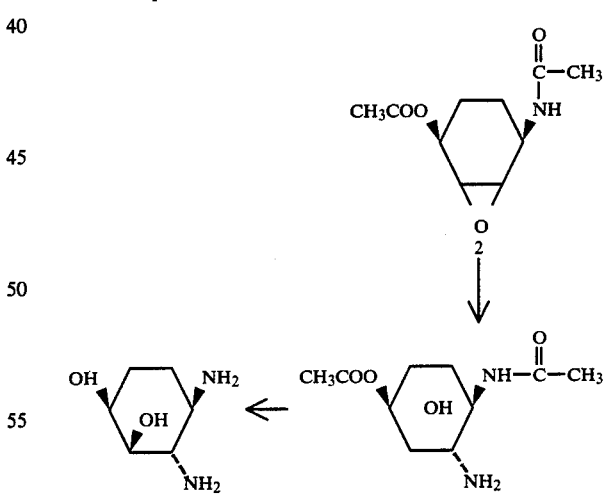

According to Scheme I, Cis-N-[4-acetyloxy-2-cyclohexene-1-yl]acetamide 1 is reacted with trifluoroacetic anhydride and hydrogen peroxide in dichloromethane at −10° to +10° C., giving the epoxide 2, which is then reacted with ammonium hydroxide in methanol at reflux, giving derivative 3, which is then heated with dilute hydrochloric acid at reflux giving the (1-α,2-α,3-β,4-α)-3,4-diamino-1,2-cyclohexanediol 4.

Scheme II

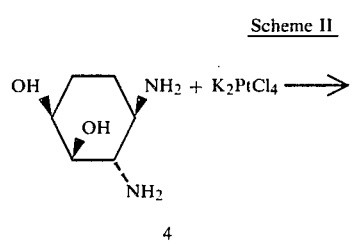

According to Scheme II the diol 4 is reacted with potassium tetrachloroplatinate in water at pH 7.0-8.0, giving dichloroplatinum complex 5.

Scheme III

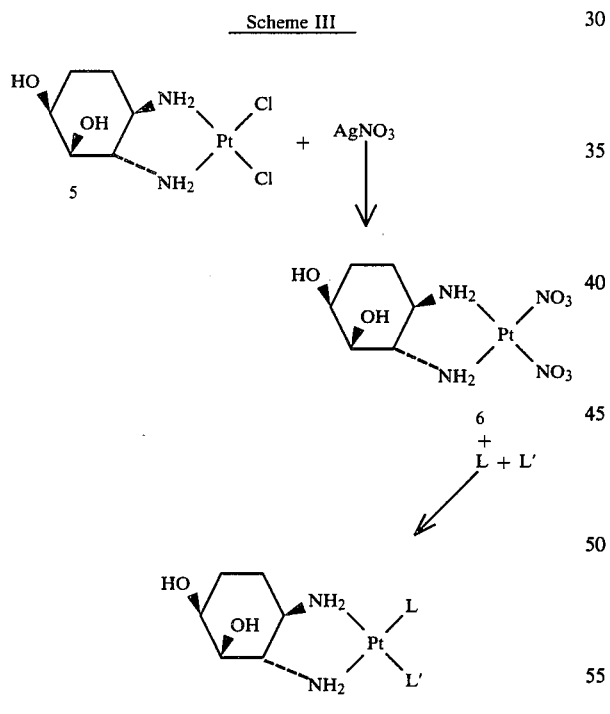

According to Scheme III, (1-α,2-α,3-β,4-α)dichloro-(3,4-diamino-1,2-cyclohexanediol-N,N')platinum 5 is reacted with silver nitrate in water giving the water soluble dinitro analog 6 which is then reacted with a di or tricarboxylic acid L+L' in water and 1N alkali, giving the products 7.

Scheme IV

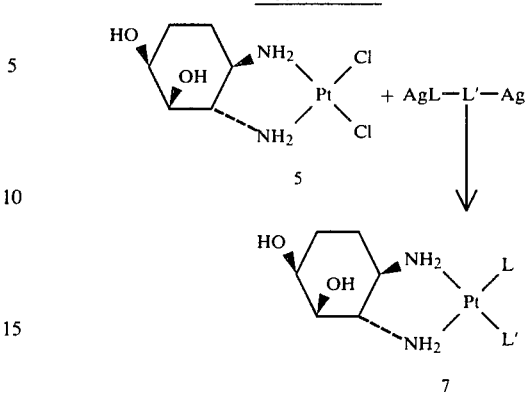

According to Scheme IV, the dichloroplatinum derivative 5 is reacted with the disilver salt of a di- or tricarboxlic acid in water, protected from light, giving the products 7.

The compounds of this invention where X is halogen or hydroxy may be prepared by reacting the product 5 or 7 with chlorine gas in dilute hydrochloric acid, giving either a tetra or dichloro derivative, or with hydrogen peroxide, giving the dihydroxy derivative.

The novel compounds of this invention possess the property of inhibiting the growth of tumors in mammals as established by the following tests.

Lymphocytic Leukemia P388 Test

The animals used were BDF/1 mice, all of one sex, weighing a minimum of 18 g and all within a 3 g weight range. There were 5 or 6 animals per test group. The tumor transplant was by intraperitoneal injection of 0.5 ml of dilute ascitic fluid containing $10^6$ cells of lymphocytic leukemia P388. The test compounds were administered intraperitoneally on days 1, 5 and 9 relative to tumor inoculation, at various doses. The animals were weighed and the survivors recorded on a regular basis for 30 days. The median survival time and the ratio of survival time for treated (T)/control (C) animals were calculated. The positive control compound was Cisplatin. The results of this test with representative compounds of this invention appear in Table I.

TABLE I

Lymphocytic Leukemia P388 Test

| Compound | Dose (mg/kg) | MST | T/C × 100 (%) |
|---|---|---|---|
| (1-α,2-α,3-β,4-α)-Dichloro(3,4-diamino-1,2-cyclohexanediol-N,N')platinum | 12.5 | 23 | 209 |
|  | 6.2 | 17 | 155 |
|  | 3.1 | 19 | 173 |
|  | 1.6 | 13 | 118 |
| Control | — | 11 | — |
| Cisplatin | 2 | 17 | 155 |
|  | 1 | 24 | 218 |
| (1-α,2-α,3-β,4-α)(3,4-Diamino-1,2-cyclohexanediol-N,N')[[2,2'-oxybis[acetato]](2-)-O¹,O¹]-platinum | 25 | 18.5 | 154 |
|  | 12.5 | 16.5 | 138 |
|  | 6.2 | 16.5 | 138 |
|  | 3.1 | 16 | 133 |
| Control | — | 12 | — |
| Cisplatin | 1 | 21.5 | 179 |
| (1-α,2-α,3-β,4-α)-(3,4-Diamino-1,2-cyclohexanediol-N,N')[[2,2'-sulfonylbis[acetato]]-O¹',O¹]-platinum | 50 | 22 | 183 |
|  | 25 | 19 | 158 |
|  | 12.5 | 17 | 142 |
|  | 6.2 | 18 | 150 |
|  | 3.1 | 15 | 125 |
| Control | — | 12 | — |
| Cisplatin | 2 | 15 | 125 |
|  | 1 | 24 | 200 |
| (1-α,2-α,3-β,4-α)-Tetrachloro- | 25 | 25 | 208 |

TABLE I-continued

Lymphocytic Leukemia P388 Test

| Compound | Dose (mg/kg) | MST | T/C × 100 (%) |
|---|---|---|---|
| (3,4-diamino-1,2-cyclohexane-diol-N,N')platinum | 12.5 | 20.5 | 171 |
|  | 6.2 | 19.5 | 163 |
|  | 3.1 | 17 | 142 |
|  | 1.6 | 14.5 | 121 |
| Control | — | 12 | — |
| Cisplatin | 2 | 15 | 125 |
|  | 1 | 24 | 200 |
| (1-α,2-α,3-β,4-β)[1,1-cyclo-butanedicarboxylato (2-)-$O^1,O^1$]-3,4-diamino-1,2-cyclohexanediol-N,N')platinum | 100 | 25 | 227 |
|  | 50 | 23 | 209 |
|  | 25 | 20 | 182 |
|  | 12.5 | 16.5 | 150 |
|  | 6.2 | 16.5 | 150 |
|  | 3.5 | 15.5 | 141 |
|  | 1.6 | 12 | 109 |
| Control | — | 11 | — |
| Cisplatin | 2 | 14 | 127 |

Melanotic Melanoma B16

The animals used were C57BC/6 mice, all of the same sex, weighing a minimum of 17 g and all within a 3 g weight range. There were 10 animals per test group. A 1 g portion of melanotic melanoma $B_{16}$ tumor was homogenized in 10 ml of cold balanced salt solution and a 0.5 ml aliquot of the homogenate was implanted intraperitoneally into each of the test mice. The test compounds were administered intraperitoneally on days 1 through 9, relative to tumor inoculation, at various doses. The animals were weighed and survivors recorded on a regular basis for 60 days. The median survival time for treated (T)/control (C) animals were calculated. The positive control compound was Cisplatin. The results of this test appear in Table II.

TABLE II

Melanotic Melanoma $B_{16}$ Test

| Compound | Dose (mg/kg) | MST | T/C × 100 (%) |
|---|---|---|---|
| (1-α,2-α,3-β,4-α)-Dichloro(3,4-diamino-1,2-cyclohexanediol-N,N')platinum | 3 | 34 | 161 |
|  | 1.5 | 32 | 152 |
|  | 0.8 | 27.5 | 131 |
| Control | — | 21 | — |
| Cisplatin | 0.4 | 31 | 147 |
|  | 0.2 | 29 | 138 |
|  | 0.1 | 30 | 143 |
| 1-α,2-α,3-β,4-α)(3,4-Diamino-cyclohexanediol-N,N')[[2,2'-oxybis[acetato]](2-)-$O^1,O^1$]-platinum | 12 | 26 | 118 |
|  | 6 | 26 | 118 |
|  | 3 | 24 | 109 |
|  | 1.5 | 26.5 | 120 |
| Control | — | 22 | — |
| Cisplatin | 0.4 | 31 | 140 |
|  | 0.2 | 30 | 136 |
|  | 0.1 | 27.5 | 125 |
|  | 0.05 | 25.5 | 116 |
| (1-α,2-α,3-β,4-α)Tetrachloro-(3,4-diamino-1,2-cyclohexane-diol-N,N')platinum | 12 | 32 | 139 |
|  | 6 | 29 | 126 |
|  | 3 | 29 | 126 |
|  | 1.5 | 26 | 113 |
| Control | — | 23 | — |
| Cisplatin | 0.4 | 32 | 139 |
|  | 0.2 | 32 | 139 |
|  | 0.1 | 29.5 | 134 |
|  | 0.05 | 29 | 117 |

Colon 26 Adenocarcinoma Test

The animals used were Balb/C mice all of one sex, weighing a minimum of 17 g and all within a 3 g weight range. There were 5 or 6 mice per test group with three groups of 5 or 6 animals used as untreated controls for each test. The tumor implant was by intraperitoneal (or subcutaneous) injection of 0.5 ml of a 2% Colon 26 tumor brei in Eagle's MEM medium containing antibiotics. The test compounds were administered intraperitoneally on days 1, 5 and 9 (relative to tumor implant doses). The mice were weighed and deaths recorded on a regular basis for 30 days. The median survival times and the ratio of survival time for treated (T)/control (C) animals were calculated. The positive control compound was Cisplatin. The results of this test on representative compounds of this invention appear in Table III.

TABLE III

Colon 26 Adenocarcinoma Test

| Compound | Dose (mg/kg) | MST | T/C × 100 (%) |
|---|---|---|---|
| (1-α,2-α,3-β,4-α)-Dichloro(3,4-diamino-1,2-cyclohexanediol-N,N')platinum | 12 | >48.5 | >230 |
|  | 6 | 30 | 143 |
|  | 3 | 25.5 | 121 |
|  | 1 | 23 | 110 |
| Control | — | 21 | — |
| Cisplatin | 1 | 36 | 171 |
|  | 0.5 | 29 | 138 |
|  | 0.25 | 28.5 | 136 |
|  | 0.125 | 26 | 124 |
| (1-α,2-α,3-β,4-α)(3,4-Diamino-1,2-cyclohexanediol-N,N')[[2,2'-oxybis[acetato]](2-)-$O^1,O^1$]-platinum | 12 | 26.5 | 158 |
|  | 6 | 21 | 123 |
| Control | — | 17 | — |
| Cisplatin | 1 | 25 | 147 |
|  | 0.5 | 23.5 | 138 |
|  | 0.25 | 27 | 158 |
| (1-α,2-α,3-β,4-α)[1,1-Cyclo-butanedicarboxylato(2-)-$O^1,O^1$]-(3,4-diamino-1,2-cyclohexanediol-N,N')platinum | 25 | 23 | 135 |
|  | 12 | 26 | 152 |
| Control | — | 17 | — |
| Cisplatin | 1 | 25 | 147 |
|  | 0.5 | 23.5 | 138 |
|  | 0.25 | 27 | 158 |

Lymphocytic Leukemia L1210 Test

The animals used BDF$_1$ of CD$_2$F$_1$ mice, all of one sex, weighing a minimum of 17 g and all within a 3 g weight range. There were 6 mice in each test group and 18 in control groups. The tumor transplant was by intraperitoneal injection of 0.5 ml of lymphocytic leukemia L1210 at a concentration of $10^5$ cells per mouse. The test compounds were administered on days 1, 5 and 9 (relative to tumor inoculation) at various doses. The mice were weighed and survivors recorded on a regular basis for 30 days. The median survival time and the ratio of survival time for treated (T)/control (C) mice were calculated. The positive control compound was Cisplatin given intraperitoneally at the indicated doses. The results of this test on representative compounds of this invention appear in Table IV.

TABLE IV

Lymphocytic Leukemia L1210 Test

| Compound | Dose (mg/kg) | MST | T/C × 100 (%) |
|---|---|---|---|
| (1-α,2-α,3-β,4-α)Dichloro(3,4-diamino-1,2-cyclohexanediol-N,N')platinum | 12.5 | 11.5 | 128 |
|  | 6.2 | 10 | 111 |
|  | 3.1 | 9.5 | 106 |
| Control | — | 9 | — |
| Cisplatin | 2 | 11 | 122 |
|  | 1 | 11.5 | 128 |
| (1-α,2-α,3-β,4-α)(3,4-Diamino-1,2-cyclohexanediol-N,N')[[2,2'-oxybis[acetato]](2-)-$O^1,O^1$]-platinum | 25 | 14.5 | 161 |
|  | 12.5 | 10.5 | 117 |
|  | 6.2 | 10 | 111 |
|  | 3.1 | 9.5 | 106 |
| Control | — | 9 | — |
| Cisplatin | 4 | 16 | 178 |
|  | 2 | 12 | 133 |

TABLE IV-continued

Lymphocytic Leukemia L1210 Test

| Compound | Dose (mg/kg) | MST | T/C × 100 (%) |
|---|---|---|---|
|  | 1 | 10 | 111 |
| (1-α,2-α,3-β,4-α)Tetachloro- | 25 | 10.5 | 117 |
| (3,4-diamino-1,2-cyclohexane- | 12.5 | 10 | 111 |
| diol-N,N')platinum | 6.2 | 10 | 111 |
|  | 3.1 | 9 | 100 |
| Control | — | 9 | — |
| Cisplatin | 4 | 13.5 | 150 |
| (1-α,2-α,3-β,4-α)[1,1-Cyclo- | 50 | 11 | 138 |
| butanedicarboxylato(2-)-O$^1$,O$^1$]- | 25 | 10 | 125 |
| (3,4-diamino-1,2-cyclohexane- | 12.5 | 9 | 113 |
| diol-N,N')platinum | 6.2 | 9 | 113 |
|  | 3.1 | 8 | 100 |
| Control | — | 8 | — |
| Cisplatin | 4 | 15 | 188 |
|  | 2 | 13 | 163 |
|  | 1 | 10 | 125 |

This aspect of the invention includes novel compositions of matter and the method of inducing the regression and/or palliation of leukemia and related cancers in mammals using the novel compounds of this invention when administered in amounts ranging from about 1 mg to about 1.2 g per square meter of body surface area per day. The interrelationship of dosages for animals of various sizes and species and humans (based on mg/m$^2$ of surface area) is described by Freireich, E. J., et al., Quantitative Comparison of Toxicity of Anticancer Agents in Mouse, Rat, Hamster, Dog, Monkey and Man. Cancer Chemother. Rep., 50, No. 4, 219–244, May 1966. A preferred dosage regimen for optimum results would be from about 3 mg/m$^2$/day to about 200 mg/m$^2$/day, and such dosage units are employed that a total of from about 5 mg to about 360 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular or subcutaneous routes.

The active compounds may be administered parenterally. Solutions or dispersions of the active compound can be prepared in water, suitably mixed with a surfactant such as hydroxypropylcellulose. Dispersions can also be prepared in glycerol, liquid polyethylene glycols, and mixtures thereof in oils. Under ordinary conditions of storage and use these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol, liquid polyethylene glycol), suitable mixtures thereof and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be obtained by the use in the compositions of agents which delay absorption, for example, aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subject to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The prinicpal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate of less frequent days. As can be seen from the dosage regimens, the amount of principal active ingredient administered is a sufficient amount to aid regression and palliation of the leukemia or the like, in the absence of excessive deleterious side effects of a cytotoxic nature to the host harboring the cancer. As used herein, cancer disease means blood malignancies such as leukemia, as well as other solid and non-solid malignancies such as the melanocarcinomas, lung carcinomas and mammary tumors. By regression and palliation is meant arresting or retarding the growth of the tumor or other manifestation of the disease compared to the course of the disease in the absence of treatment.

This invention will be described in greater detail in conjuction with the following non-limiting specific examples.

EXAMPLE 1

(1-α,2-α,3-β,4-α)-3,4-Diamino-1,2-cyclohexanediol

To a solution of 6.1 g of 1-chloro-1-nitrosocyclohexane in 135 ml of ethanol and 260 ml of carbon tetrachloride, cooled to −20° C. in an acetone-dry ice bath, was slowly added 33.6 ml of 1,3-cyclohexadiene. The mixture was stored at −20° C. for 6 days and the solid collected, giving 4.5 g of 2-oxa-3-azabicyclo[2.2.2]oct-5-ene, hydrochloride.

A solution of 1.0 g of the above compound in 50 ml of water was cooled in an ice bath to 0° C., then 3.3 g of zinc dust was added. Concentrated hydrochloric acid was added dropwise, keeping the reaction temperature below 10° C. When hydrogen evolution ceased an additional 24 g of zinc dust was added over 4 hours along with a total of 85 ml of concentrated hydrochloric acid. The mixture was filtered and the pH of the filtrate adjusted to 8 with 10N sodium hydroxide and cooling. This mixture was filtered and the filtrate evaporated to dryness in vacuo. The residue was triturated with chloroform. The chloroform extract was evaporated to dryness and the residue washed with ether, giving 250 mg of cis-4-amino-2-cyclohexene-1-ol.

A solution of 350 mg of cis-4-amino-2-cyclohexene-1-ol in 5 ml of acetic anhydride and 0.5 ml of pyridine was stored at room temperature overnight. The solution was evaporated to dryness in vacuo and the residue was crystallized by dissolving in 5 ml of hot ethyl acetate and adding 7 ml of hexane, yield 460 mg of cis-N-[4-(acetyloxy)-2-cyclohexene-1-yl]acetamide.

A 15.1 ml portion of trifluoroacetic anhydride was added to 69 ml of dichloromethane which was cooled in an ice bath. To this was slowly added 3.7 ml of 75% hydrogen peroxide. This solution was slowly added to a solution of 5.5 g of cis-N-[4-(acetyloxy-2-cyclohexene-1-yl]acetamide in 69 ml of dichloromethane, then 22 g of sodium carbonate and 39 ml of water, all while cooling in an ice bath. The mixture was stirred at 0° C. for 2 hours, then the organic layer was separated and saved. The aqueous layer was extracted with 25 ml of dichloromethane. The organic phases were combined, evaporated and recrystallized from methanol-hexane, giving a 4.5 g of N-[5-(acetyloxy)-7-oxabicyclo[4.1.0]hept-2-yl]-(1-α,2-α,5-β,6-α)acetamide.

A solution of 1.0 g of the above compound in 50 ml of methanol and 50 ml of concentrated ammonium hydroxide was heated at reflux for 12 hours, then 50 ml of concentrated ammonium hydroxide was added and refluxing was continued for 8 hours. An additional 50 ml of concentrated ammonium hydroxide was introduced, the mixture was allowed to stand overnight and then evaporated to dryness in vacuo.

A solution of the above residue in 75 ml of 9% aqueous hydrochloric acid was heated at reflux for 6 hours and then evaporated to dryness, giving 1 g of the desired product.

EXAMPLE 2

(1-α,2-α,3-β,4-α)-Dichloro(3,4-diamino-1,2-cyclohexanediol-N,N')platinum

A solution of 1 g of (1-α,2-α,3-β,4-α)-3,4-diamino-1,2-cyclohexandiol in 75 ml of water was adjusted pH 7.9 with an ion exchange resin. This solution was filtered into a solution of 1.86 g of potassium tetrachloroplatinate in 50 ml of water and then stirred for 6 hours. The resulting solid was collected, giving 300 mg of the desired product, mp 240° C.

EXAMPLE 3

(1-α,2-α,3-β,4-α)-(3,4-Diamino-1,2-cyclohexanediol-N,N')[[2,2'oxybis[acetato]](2-)-O$^1$,O$^1$]platinum To a suspension of 250 mg of (1-α,2-α,3-β,4-α)-dichloro(3,4-diamino-1,2-cyclohexanediol-N,N')platinum in 20 ml of water was added 202 mg of silver nitrate. This mixture was stirred for 3 hours and then filtered. To the filtrate was added a solution of 80 mg of diglycolic acid in 10 ml of water and 1.6 ml of 1N sodium hydroxide. This mixture was stirred for 2 hours, then evaporated to 10 ml and poured into 50 ml of ethanol. The resulting solid was collected, giving 255 mg of the desired product, mp 230° C. (dec.).

EXAMPLE 4

(1-α,2-α,3-β,4-α)(3,4-Diamino-1,2-cyclohexanediol-N,N')[[2,2'-sulfonylbis[acetato]](2-)-O$^1$,O$^1$]platinum To a solution of 25 mg of (1-α,2-α,3-β,4-α)-dichloro(3,4-diamino-1,2-cyclohexanediol-N,N')platinum in 75 ml of water was added 24 mg of the disilver salt of sulfonyldiacetic acid. This mixture was stirred overnight and then filtered. The filtrate was evaporated to dryness, giving 16 mg of the desired product, mp>260° C.

EXAMPLE 5

(1-α,2-α,3-β,4-α)Tetrachloro(3,4-diamono-1,2-cyclohexanediol-N,N')platinum

Chlorine gas was passed into a suspension of 230 mg of (1-α,2-α,3-β,4-α)-dichloro(3,4-diamino-1,2-cyclohexanediol-N,N')platinum in 20 ml of 0.5N hydrochoric acid at 90° C. The application of chlorine gas was continued for 8 hours with the solution held at 90° C. for the first 2 hours. Nitrogen was the bubbled into the solution to displace the free chlorine, then the solvent was evaporated in vacuo, giving 230 mg of the desired product, mp 240° C. (dec.).

EXAMPLE 6

(1-α,2-α,3-β,4-α)[1,1-Cyclobutanedicarboxylato(2-)-O$^1$,O$^1$](3,4-diamino-1,2-cyclohexanediol-N,N')platinum To a suspension of 257 mg of (1-α,2-α,3-β,4-α)-dichloro(3,4-diamino-1,2-cyclohexanediol-N,N')platinum in 20 ml of water was added 210 mg of silver nitrate. This mixture was stirred for 3 hours and then filtered. To the filtrate was added a solution of 89 mg of 1,1-cyclobutanedicarboxylic acid in 10 ml of water and 1.2 ml of 1N sodium hydroxide. This mixture was stirred for 2 hours and then evaporated to dryness. The residue was treated with 4 ml of ice water and filtered, giving 150 mg of the desired product, mp>260° C.

EXAMPLE 7

(1-α,2-α,3-β,4-α)(3,4-Diamino-1,2-cyclohexanediol-N,N')[1,1,2-ethanetricarboxylato(2-)-O¹,O¹]platinum To a solution of 31 mg of (1-α,2-α,3-β,4-α)-dichloro(3,4-diamino-1,2-cyclohexanediol-N,N')platinum in 50 ml of water was added 28 mg of the disilver salt of 1,1,2-ethanetricarboxylic acid. This mixture was stirred in the dark for 24 hours, then filtered and the filtrate evaporated to dryness, giving 16 mg of the desired product, mp 230° C.

We claim:
1. A compound selected from those of the formulae:

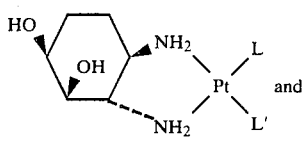
and
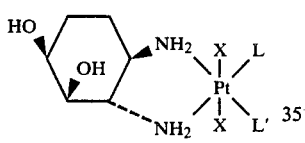

wherein L and L' are selected from the group consisting of halide, nitrate, sulfate and a monobasic carboxylate such as acetate or hydroxy acetate or L and L' taken together may be a dibasic carboxylate selected from the group consisting of

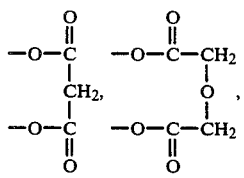

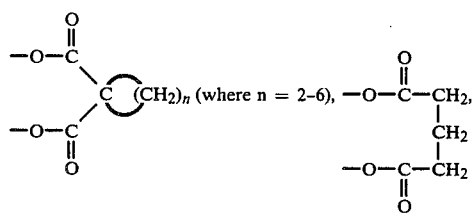

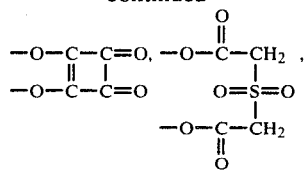

oxalic acid, methylmalonic acid, succinic acid, or L and L' taken together may be a tribasic carboxylate selected from the group consisting of

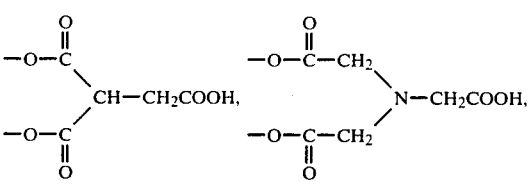

and

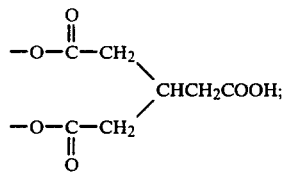

and X is selected from the group consisting of halogen and hydroxy.

2. The compound according to claim 1, (1-α,2-α,3-β,4-α)-dichloro(3,4-diamino-1,2-cyclohexanediol-N,N')platinum.

3. The compound according to claim 1, (1-α,2-α,3-β,4-α)(3,4-diamino-1,2-cyclohexanediol-N,N')[[2,2'-oxybis[acetato]](2-)-O¹,O¹]platinum.

4. The compound according to claim 1, (1-α,2-α,3-β,4-α)[1,1-cyclobutanedicarboxylato(2-)-O¹,O¹](3,4-diamino-1,2-cyclohexanediol-N,N')platinum.

5. The compound according to claim 1, (1-α,2-α,3-β,4-α)(3,4-diamino-1,2-cyclohexanediol-N,N')-[[2,2'-sulfonybis[acetato]](2-)-O¹,O¹]platinum.

6. The compound according to claim 1, (1-α,2-α,3-β,4-α)(3,4-diamino-1,2-cyclohexanediol-N,N')[1,1,2-ethanetricarboxylato(2-)-O¹,O¹]platinum.

7. The compound according to claim 1, (1-α,2-α,3-β,4-α)(3,4-diamino-1,2-cyclohexanediol-N,N')platinum.

8. A composition of matter in dosage unit form comprising from about 1 mg to about 1.2 g per square meter of mammalian body surface area of a compound of claim 1 in association with a pharmaceutically acceptable carrier.

* * * * *